(12) United States Patent
Bastioli et al.

(10) Patent No.: US 9,862,671 B2
(45) Date of Patent: Jan. 9, 2018

(54) PROCESS FOR THE SYNTHESIS OF ALIPHATIC DIALKYL ESTERS FROM VEGETABLE OILS

(71) Applicant: NOVAMONT S.P.A., Novara (IT)

(72) Inventors: Catia Bastioli, Novara (IT); Luigi Capuzzi, Novara (IT); Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 15/124,876

(22) PCT Filed: Mar. 10, 2015

(86) PCT No.: PCT/EP2015/054938
§ 371 (c)(1),
(2) Date: Sep. 9, 2016

(87) PCT Pub. No.: WO2015/135929
PCT Pub. Date: Sep. 17, 2015

(65) Prior Publication Data
US 2017/0121266 A1    May 4, 2017

(30) Foreign Application Priority Data
Mar. 11, 2014  (IT) .............................. MI2014A0374

(51) Int. Cl.
*C07C 69/34*   (2006.01)
*C07C 67/03*   (2006.01)
*C07C 67/48*   (2006.01)

(52) U.S. Cl.
CPC .............. *C07C 67/03* (2013.01); *C07C 67/48* (2013.01)

(58) Field of Classification Search
CPC ......... C07C 67/03; C07C 67/48; C07C 67/08; C07C 67/31; C07C 67/313; C07C 69/34; C07C 69/48; C07C 69/675
See application file for complete search history.

(56) References Cited

FOREIGN PATENT DOCUMENTS

| WO | WO-2008/138892 A1 | 11/2008 |
| WO | WO2008138892 | * 11/2008 |
| WO | WO-2011/080296 A1 | 7/2011 |
| WO | WO-2012/085012 A2 | 6/2012 |
| WO | WO2012085012 | * 6/2012 |
| WO | WO-2013/189915 A1 | 12/2013 |
| WO | WO2013189915 | * 12/2013 |
| WO | WO2012085012 | * 6/2016 |

* cited by examiner

*Primary Examiner* — Yevegeny Valenrod
*Assistant Examiner* — Blaine G Doletski
(74) *Attorney, Agent, or Firm* — Polsinelli PC

(57) ABSTRACT

This invention relates to a process for obtaining highly pure aliphatic dialkyl esters of saturated dicarboxylic acids from vegetable oils, which can advantageously be used in polymerization. The process comprises the steps of reacting with an aliphatic alcohol a triglycerides mixture containing at least one triglyceride of at least one saturated dicarboxylic acid in the presence of one or more catalysts capable of catalyzing the esterification and transesterification reactions, and separating the dialkyl esters of saturated dicarboxylic acids from the reaction mixture thus obtained.

20 Claims, 2 Drawing Sheets

PROCESS FOR THE SYNTHESIS OF ALIPHATIC DIALKYL ESTERS FROM VEGETABLE OILS

CROSS REFERENCE TO RELATED APPLICATIONS

This application is a National Phase filing under 35 U.S.C. §371 of PCT/EP2015/054938 filed on Mar. 10, 2015; and this application claims priority to Application No. MI2014A000374 filed in Italy on Mar. 11, 2014 under 35 U.S.C. §119. The entire contents of each application are hereby incorporated by reference.

This invention relates to a process for obtaining saturated aliphatic dialkyl esters comprising the step 1) of reacting a triglycerides mixture containing at least a triglyceride of at least one saturated dicarboxylic acid with an aliphatic alcohol in the presence of one or more catalysts capable of catalysing the esterification and transesterification reactions, and the step 2) of separating the aliphatic dialkyl esters of dicarboxylic acids from the reaction mixture obtained at the end of step 1).

The process according to this invention makes it possible to obtain highly pure saturated dicarboxylic acid derivatives from vegetable oils, which can advantageously be used for polymerisation, simply and economically.

Patent Applications WO 2008/138892 and WO 2011/080296 describe batch and continuous processes for obtaining dicarboxylic acids, in particular azelaic acid, from vegetable oils. In these processes, after the monocarboxylic acids obtained by oxidative cleavage of the double bonds have been separated out, the triglycerides containing azelaic acids are subjected to hydrolysis and subsequent treatments to separate the azelaic acid from the glycerine and the long chain saturated monocarboxylic acids initially present in the triglycerides which are released during the hydrolysis reaction.

WO 2008/138892 describes a series of hot water extractions to separate azelaic acid and glycerine from the saturated monocarboxylic acids, followed by crystallisation of the acid by cooling the aqueous solution. In WO 2011/080296 the glycerine is separated out by centrifuging the aqueous phase, and subsequently the organic phase containing azelaic acid undergoes thin film evaporation and distillation in a column to separate the azelaic acid from the saturated monocarboxylic acids.

However the first process has the disadvantage that it requires very large quantities of water for the extraction of azelaic acid, whose non-negligible solubility in water, even at ambient temperature, helps to reduce the yield of product recovery; the second process requires complex and costly operations to purify the azelaic acid from long chain saturated monocarboxylic acids such as palmitic and stearic acids which interfere should it be used in polymerisation reactions.

Processes of esterification of triglycerides mixtures containing triglycerides of dicarboxylic acids are described to prepare oligomeric structures in the patent applications WO 2012/085012 and WO 2013/189915. Limited amounts of alkyl esters are therein obtained as by-products.

With the process according to this invention it is instead possible to obtain dicarboxylic acid derivatives such as aliphatic dialkyl esters from vegetable oils in high yields and with high purity, and these can readily be used for polymerisation reactions.

These aliphatic dialkyl esters are readily separated from glycerine and long chain acid monoesters, appreciably simplifying the operations of separating the products. This also makes it possible to recover high concentrations of the glycerine obtained as a by-product.

This invention relates in particular to a process for the production of aliphatic dialkyl esters in which triglycerides containing dicarboxylic acids undergo a reaction esterifying the free carboxyl groups and a reaction transesterifying the carboxyl groups bound to the glycerol. Depending upon the catalysts selected, it is possible for these reactions to be performed simultaneously or separately in two successive stages.

Figure 1:
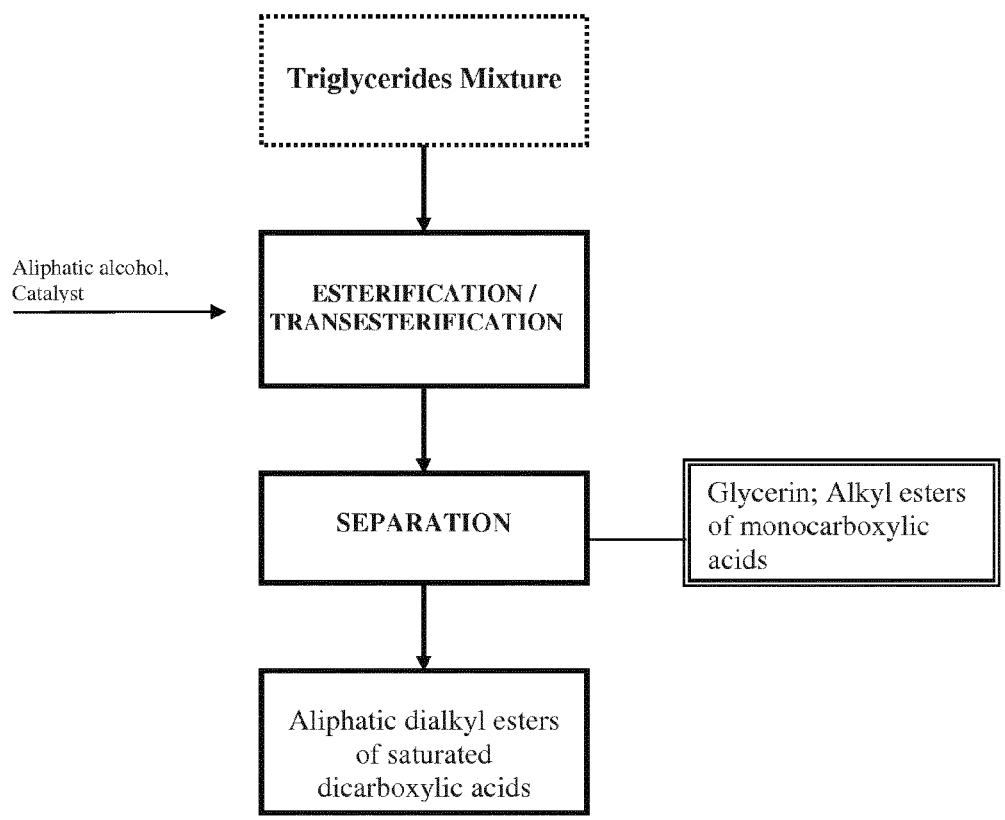
FIG. 1 shows a flow diagram of the process according to the invention.
Figure 2:
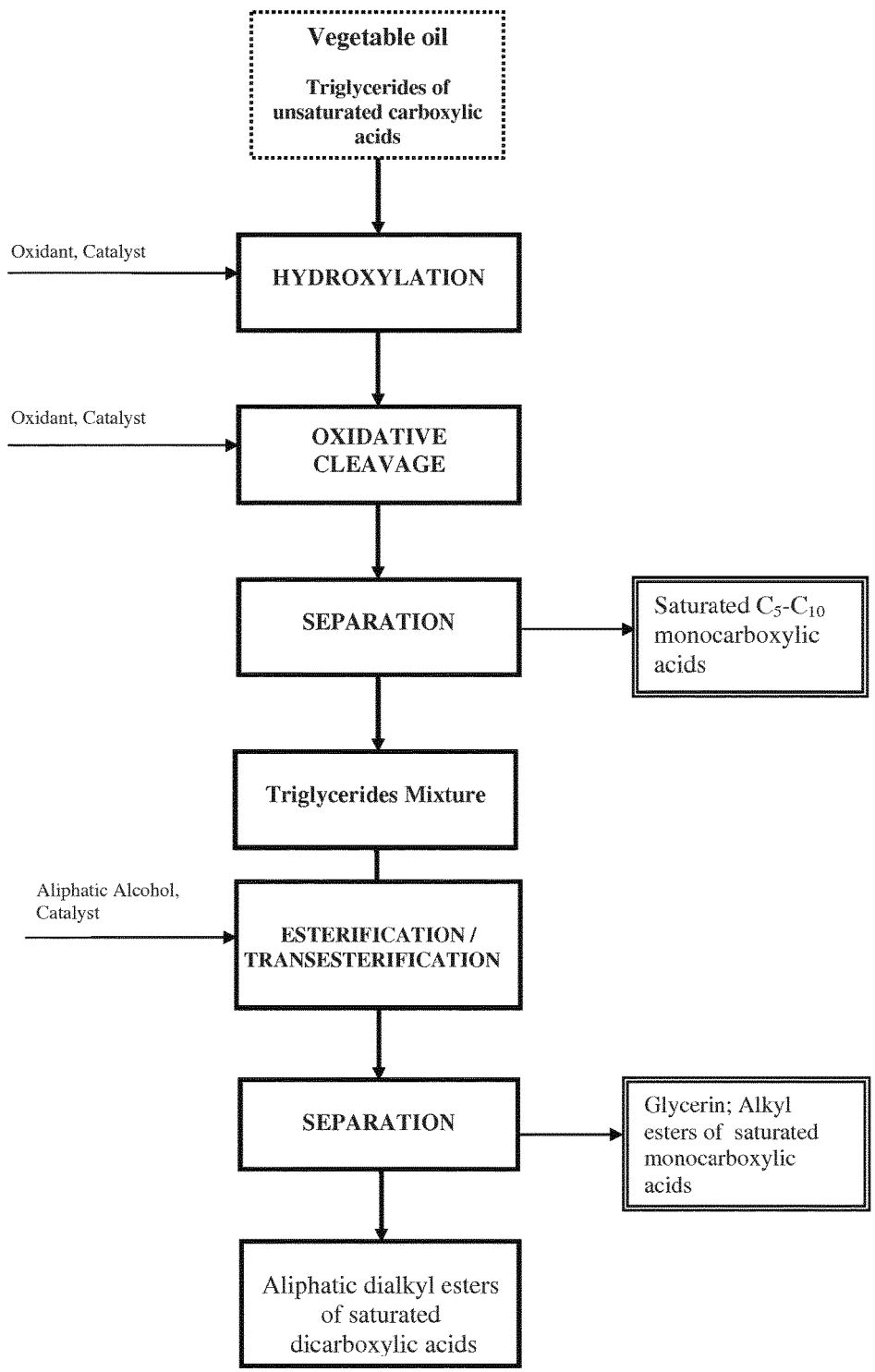
FIG. 2 shows a flow diagram of a preferred embodiment of the process according to the invention which includes three preliminary steps to obtain triglycerides containing at least one dicarboxylic acid (steps a), b), c)).

Object of the present invention is a process for preparing aliphatic dialkyl esters of saturated dicarboxylic acids from a triglycerides mixture containing
- at least one triglyceride of at least one saturated dicarboxylic acid and
- at least 65% of glycerides of formula $R_x$—O—$CH_2$—CH($OR_y$)—$CH_2$—O—$R_z$,
- wherein $R_x$, $R_y$, $R_z$ are independently selected from the group consisting of H, $C_6$-$C_{24}$ monocarboxylic acid residues and $C_6$-$C_{24}$ dicarboxylic acid residues, and wherein at least one of $R_x$, $R_y$, $R_z$ is a $C_6$-$C_{24}$ dicarboxylic acid residue, comprising the steps of:
1) reacting with an aliphatic alcohol the said triglycerides mixture, in the presence of one or more catalysts capable of catalysing the esterification and/or transesterification reactions;
2) separating the aliphatic dialkyl esters of saturated dicarboxylic acids from the reaction mixture obtained at the end of step 1).

The percentage content of the above mentioned glycerides is intended as the % area measured by HPLC-MS analysis operating in gradient mode with ESI (+/−) ionization, using a Mass Spectrometer equipped with a Kinetex Phenomenex 2.6 μm C8 100 Å 100×2.1 mm column at 40° C. and PDA detector, with Formic acid 1% (A) and $CH_3CN$ (B) as solvent and the following gradient: 0 min (A/B=80/20), 2 min (A/B=80/20), 40 min (A/B=5/95), 50 min (A/B=5/95), 55 min (A/B=80/20); flow 0.5 ml/min; Full scan 100-2000 Da.

The reaction mixture obtained at the end of step 1) contains glycerine, aliphatic dialkylesters of dicarboxylic acids and possibly aliphatic esters of monocarboxylic acids present in the starting triglycerides. Step 2) is intended to separate the said aliphatic dialkyl esters of dicarboxylic acids from the glycerine and the said aliphatic esters of monocarboxylic acids.

The peculiar composition of the starting triglycerides mixture allows to provide the separated aliphatic dialkylesters of saturated dicarboxylic acids in particularly high yields. Advantageously, the said yield is equal to or greater than 60% by weight with respect to the theoretical dicarboxylic acid content of the triglycerides mixture of step 1). More advantageously, said yield is equal to or greater than 70% by weight.

The at least one triglyceride of at least one dicarboxylic acid which undergoes the esterification and transesterification reactions of step 1) of this process is a triglyceride in which one or more of the oxygens in the hydroxyl groups of the glycerol residue are bound to an aliphatic dicarboxylic acid residue.

Where one molecule of triglyceride contains two or three dicarboxylic acid residues, these dicarboxylic acid residues may be the same or different.

The said dicarboxylic acids are saturated and are preferably of the alpha-omega type.

In step 1) of the process the triglycerides of at least one dicarboxylic acid are caused to react with one or more aliphatic alcohols.

Typical examples of aliphatic alcohols are linear or branched chain $C_1$-$C_{10}$ monoalcohols. $C_1$-$C_8$ alcohols are preferred and $C_1$-$C_4$ alcohols are even more preferred. Advantageously primary alcohols are used. Examples of preferred alcohols are methanol, ethanol, n-propanol and n-butanol. More preferably n-butanol is used.

The esterification and transesterification reactions performed in the course of step 1) of this process may be performed simultaneously in a single stage or in two successive stages.

When the reaction of esterifying the free acid groups and the reaction of transesterifying the acid groups bound to the glycerol are performed simultaneously, a strong acid is used as the catalyst for step 1).

For the purposes of this invention, the strong acid is preferably selected from hydrochloric acid, sulfuric acid, perchloric acid, hydrobromic acid, hydroiodic acid, nitric acid, alkylsulfonic acids, arylsulfonic acids, sulfonic resins or acid earths such as montmorillonites of the KSF type, and Bronsted inorganic or organic acids having a dissociation constant $Ka>55$ ($pKa<-1.74$) at 25° C. The catalyst is more preferably selected from hydrochloric acid, sulfuric acid, perchloric acid, hydrobromic acid, hydroiodic acid, nitric acid, alkylsulfonic acids, arylsulfonic acids, sulfonic resins or acid earths such as montmorillonites of the KSF type.

The quantity of catalyst may vary depending upon the type of acid preselected and in general comprises between 0.1 and 5% by weight with respect to the mixture which has to be esterified.

The simultaneous esterification and transesterification reaction is performed using an excess of aliphatic alcohol with respect to the carboxylic groups present in the mixture at an internal temperature preferably comprised between 80° C. and the reflux temperature of the alcohol in the reaction mixture, which is normally up to a maximum of 200° C., and removing the water which forms in the course of the esterification.

Those skilled in the art will be capable of identifying suitable temperature conditions on the basis of the quantity and type of alcohol present. In the case of n-butanol a temperature of between 80 and 160° C., preferably between 120° C. and 150° C., is used.

On completion of the reaction the excess alcohol is distilled off under vacuum at a temperature of preferably between 50-100° C.

When the reaction for esterification of the free acid groups is performed separately with respect to the reaction for transesterification of the acid groups bound to the glycerol, it is necessary to use a weak acid as the catalyst for the first stage in step 1) (i.e. the reaction of esterifying the free acid groups).

For the purposes of this invention, the weak acid is different from the strong acids and is preferably selected from phosphoric acid, tungstic acid, molybdic acid, phosphotungstic acid, weakly acid montmorillonites (for example of the K-10 type), and organic or inorganic Bronsted acids having a dissociation constant or constants of $Ka \leq 1 \times 10^{-2}$ ($pKa \geq 2$) at 25° C.

Preferably the esterification catalyst is selected from phosphoric acid, tungstic acid, molybdic acid, phosphotungstic acid or weakly acid montmorillonites (for example of the K-10 type).

The quantity of catalyst may vary depending upon the type of acid preselected and in general lies between 0.1 and 5% by weight with respect to the mixture which has to be esterified.

The esterification reaction is performed using a quantity of aliphatic alcohol which is sufficient to esterify the free carboxylic groups present in the mixture at a temperature which normally corresponds to that of the boiling point of the alcohol, preferably between 80 and 200° C., and removing the water which forms in the course of the reaction.

On completion of the conversion the temperature is adjusted to a value below the boiling point of the alcohol, a strong base is added together with excess alcohol or in any event a sufficient quantity to transesterify with the glycerine, and the temperature is adjusted to the reflux temperature of the mixture for the time required to complete the reaction (second substage in step 1).

The strong base used as a catalyst for the second substage in step 1) (i.e. transesterification of the acid groups bound to the glycerol) is preferably selected from the group comprising alkali hydroxides (sodium hydroxide, potassium hydroxide) and alkali alkoxides (sodium methylate, potassium t-butylate).

The quantity of base may depend according to the type selected and should be in sufficient quantity to neutralise the acid catalyst used during the esterification stage and catalyse the subsequent transesterification; this in general lies between 0.2 and 10% by weight with respect to the mixture which has to be esterified.

On completion of the reaction the excess alcohol is distilled off under vacuum at a temperature of preferably between 50 and 100° C.

Separation of the glycerine in step 2) of the process according to the invention may take place in different manners depending on how step 1) is performed.

In the first case (i.e. step 1 performed in a single stage), after the excess alcohol has been distilled off most of the glycerine separates out from the oily phase containing the mixture of aliphatic esters as a result of cooling to ambient temperature and is recovered by, for example, settling. The oily phase is washed with water to reduce the acidity and remove the remaining glycerine, and after neutralisation and concentration of the water it can be recovered and pooled with that obtained previously.

In the second case (i.e. step 1 performed in two stages), the distillation residue is normally washed with water to recover the glycerine and dehydrated.

In any event, once the glycerine has been separated off the remaining reaction mixture mainly contains aliphatic diesters of dicarboxylic acids.

Depending upon the composition of the starting material, the reaction mixture may also contain monocarboxylic acid esters formed following the transesterification reaction, in addition to a reaction residue containing oligomers.

The dicarboxylic acid diesters are therefore separated from such monocarboxylic acid monoesters, advantageously by distillation under high vacuum conditions.

The diesters obtained at the end of step 2) are particularly suitable for use in polymerisation.

If used in polymerisation the said diesters may advantageously undergo preliminary transesterification treatments with diols, for example with butandiol.

The starting material suitable for this process is a triglycerides mixture comprising one or more triglycerides containing at least one dicarboxylic acid, which may be the same or different. The said triglycerides mixture comprises also at least 65%, preferably at least 70%, more preferably at least 75%, even more preferably at least 80% of glycerides of formula $R_x$—O—$CH_2$—$CH(OR_y)$—$CH_2$—O—$R_z$, wherein $R_x$, $R_y$, $R_z$ are independently selected from the group consisting of H, $C_6$-$C_{24}$ monocarboxylic acid residues and $C_6$-$C_{24}$ dicarboxylic acid residues, and wherein at least one, preferably at least two of $R_x$, $R_y$, $R_z$ are $C_6$-$C_{24}$ dicarboxylic acid residues.

By $C_6$-$C_{24}$ dicarboxylic acids are meant aliphatic diacids, preferably of the alpha-omega type. Suberic acid, azelaic acid, brassylic acid and their mixtures are particularly preferred.

By $C_6$-$C_{24}$ monocarboxylic acids are meant aliphatic monoacids which may be saturated or unsaturated and substituted or unsubstituted.

Preferred unsubstituted monocarboxylic acids are monoacids having a chain length of $C_{9-24}$; palmitic, stearic, oleic, arachidic, behenic and lignoceric acids are particularly preferred.

When substituted monocarboxylic acid residues are present, long chain monocarboxylic acids having one or more ketone groups and/or hydroxyl groups in non-terminal positions are preferred, and among these $C_{12}$-$C_{24}$ hydroxy acids containing at least one secondary hydroxyl group are particularly preferred. Examples of substituted monocarboxylic acids which may be present are 9-hydroxystearic acid, 9-ketostearic acid, 10-ketostearic acid, 10-hydroxystearic acid, dihydroxypalmitic acid, dihydroxystearic acid, dihydroxyoleic acid, dihydroxyarachidic acid and dihydroxybehenic acid.

The content of glycerides with carboxylic acid residues bearing keto groups is preferably below 10% (HPLC-MS area). According to a preferred embodiment, the said mixture comprises less than 5% of glycerides with carboxylic acid residues bearing keto groups.

The Number Average Molecular Weight (Mn) of the said triglycerides mixture is advantageously less than 400 Da when measured by GPC analysis after calibration with polystyrene standard.

The said triglycerides containing at least one dicarboxylic acid may advantageously be obtained from vegetable oils containing unsaturated carboxylic acids using known means. One example is oxidative reactions cleaving the double bonds present in the unsaturated carboxylic acids. These reactions may be performed using one or more oxidising agents such as for example inorganic and organic peroxides, peracids, nitric acid, permanganates, periodates, $O_2$, $O_3$ or mixtures of gases containing them.

In particular the mixtures of triglycerides obtained by oxidative cleavage processes of vegetable oils using peroxides, such as hydrogen peroxide, and $O_2$ or mixtures containing $O_2$ are advantageously used as a starting material for this process. Preferred examples are the processes described in applications WO 2008/138892, WO 2011/080296 or WO 2013/079849 A1.

Mixtures of triglycerides containing dicarboxylic acids obtained after step c) of separating out saturated monocarboxylic acids by means of the processes described in applications WO 2008/138892 and WO 2011/080296 are particularly preferred.

According to a preferred embodiment, the triglycerides containing at least one saturated dicarboxylic acid according to this invention are prepared from vegetable oils containing triglycerides of unsaturated carboxylic acids by means of a process comprising the steps of:
  a) causing the unsaturated carboxylic acid triglycerides to react with an oxidising compound in the presence of a catalyst capable of catalysing the reaction of oxidising the olefin double bond to obtain an intermediate compound containing vicinal diols;
  b) causing the said intermediate compound to react with oxygen, or a gaseous mixture containing oxygen, and a catalyst capable of catalysing the reaction of oxidising the vicinal diols to carboxyl groups in order to obtain (i) saturated monocarboxylic acids and (ii) triglycerides containing saturated dicarboxylic acids;
  c) separating the saturated monocarboxylic acids (i) from the triglycerides containing saturated dicarboxylic acids (ii).

By vegetable oils containing unsaturated carboxylic acids are meant either the unmodified product of pressing, or an oil which has undergone chemical or chemical and physical modifications such as for example purification treatments or enzyme enrichment. Examples of vegetable oils are: soya oil, olive oil, castor oil, sunflower oil, thistle oil, safflower oil, peanut oil, maize oil, palm oil, jatropha oil, cuphea seed oil, oils from Brassicaceae such as *Crambe abyssinica, Brassica carinata, Brassica napus* (colza), *Lesquerella*, and other oils having a high monounsaturated acids content. The use of sunflower oil, thistle oil and oils from Brassicaceae is particularly preferred. Even more preferred is the use of sunflower oil and thistle oil having a high content of oleic acid and oils from Brassicaceae having a high content of erucic acid.

The triglycerides may contain both monounsaturated and polyunsaturated carboxylic acids. Examples of unsaturated carboxylic acids are: 9-tetradecenoic (myristoleic) acid, 9-hexadecenoic (palmitoleic) acid, 9-octadecenoic (oleic) acid, 12-hydroxy-9-octadecenoic (ricinoleic) acid, 9-eicosenoic (gadoleic) acid, 13-docosenoic (erucic) acid, 15-tetracosenoic (nervonic) acid, 9,12-octadecadienoic (linoleic) acid and 9,12,15-octadecatrienoic (linolenic) acid.

Monounsaturated carboxylic acids are particularly preferred. The use of oleic acid and erucic acid is particularly advantageous in the process according to the invention.

As mentioned, the starting triglycerides normally also contain saturated monocarboxylic acids which remain bound to the glycerine together with the dicarboxylic acids (ii) at the end of step c). Generally the triglycerides present in the starting oils contain medium-long chain saturated monocarboxylic acids, i.e. those with a chain length of $C_5$ or more. The oils preferably used may contain triglycerides of long chain saturated monocarboxylic acids, i.e. those of $C_{12}$ or more, preferably $C_{14}$-$C_{24}$.

In one form of the process for preparing triglycerides containing saturated dicarboxylic acids according to the invention, the catalyst is not removed at the end of step a).

In a preferred form, step b) is performed without the addition of water other than that in which the catalyst is dissolved. Advantageously the said step b) comprises an aqueous phase and an organic phase with a water/diol ratio of less than 1:3.

The oxidising substance used to perform step a) is preferably an aqueous solution of hydrogen peroxide having concentrations between 30 and 80%, preferably between 40 and 70% and even more preferably between 49 and 65%.

In step b) the diol resulting from step a) is caused to react with oxygen or a gaseous mixture containing oxygen. The use of air is particularly advantageous. Oxygen-enriched air may also be used.

The catalyst in step a) belongs to the group of transition elements. Fe, Mn, Mo, Nb, Os, Re, Ti, V, W, Zr and their acids, alkaline salts and complexes are advantageously used as homogeneous or heterogeneous phase catalysts, possibly in supported or nanostructured form. The use of tungstic acid or phosphotungstic acid is particularly preferred. This catalyst is present in quantities of between 0.03% and 3% in moles, preferably between 0.05% and 1.8% in moles and even more preferably between 0.06% and 1.5% in moles with respect to the total moles of unsaturated compounds. In a preferred form of the process the catalyst may be fed in the form of a solution in a non-organic solvent.

As far as the catalyst for step b) is concerned, this belongs to the group of transition elements. Ce, Cr, Co, Cu, Mn, Mo, Re, Os, V and W and their acids, alkaline salts and complexes are advantageously used as homogeneous or heterogeneous phase catalysts, possibly in supported or nanostructured form. The use of cobalt salts, such as for example acetate, chloride, sulfate, bromide and nitrate, used in quantities between 0.05% and 3% in moles, preferably between 0.1% and 2% in moles and even more preferably between 0.3% and 1.5% in moles with respect to the diol produced during step a) is particularly preferred. The use of cobalt acetate and cobalt chloride is particularly preferred.

An inorganic acid may be added to the catalyst in step b). Examples of inorganic acids are phosphoric acid, sulfuric acid, hydrochloric acid, perchloric acid and their mixtures.

A small quantity of the intermediate compound obtained at the end of step a) may be added when starting step a) given that the diols present in it encourage activation of the reaction. This intermediate compound may be added in a quantity of ≤5%, preferably ≤3% by weight with respect to the starting oil.

Advantageously, nitrogen or air are caused to flow through in the course of step a) to remove part of the water produced in the process. In this way excessive dilution of $H_2O_2$ is avoided. An alternative to a flow of these gases is evaporation under vacuum.

The reaction temperature for step a) and step b) advantageously lies between 45 and 95° C., preferably between 50 and 90° C.

The reaction temperature in step a) advantageously lies between 55 and 80° C.

The reaction temperature in step b) advantageously lies between 55 and 90° C., even more advantageously between 60 and 70° C.

Advantageously, the average residence time in the reactor for performing both step a) and step b) is between 2 and 8 hours.

In a preferred form of the process the intermediate product resulting from step a) is fed directly to the reactor in which step b) is carried out.

Step a) is preferably carried out at atmospheric pressure or under slight vacuum.

Step b) is preferably carried out with air at a pressure of ≤50 atm, preferably ≤25 atm.

Advantageously the aqueous phase is separated from the organic phase at the end of step b). The aqueous phase contains the catalysts for steps a) and b) which can be recovered and optionally recycled as catalysts for step b). The organic phase is a clear oil comprising a mixture comprising substantially (i) free saturated monocarboxylic acids formed by the process of oxidative cleavage, and (ii) triglycerides containing saturated dicarboxylic acids, saturated monocarboxylic acids present in the starting mixture, and possibly dihydroxycarboxylic acids (vicinal diols) formed at the end of step a) and not converted in the course of step b).

In a preferred form of the process in which oil having a high oleic acid content is used as a starting material, the organic phase substantially comprises pelargonic acid and triglycerides of azelaic, palmitic, stearic and dihydroxystearic acids.

In another preferred form of the process in which oils having a high erucic acid content are used as a starting material the organic phase substantially comprises pelargonic acid and triglycerides of azelaic, brassylic, palmitic, stearic, dihydroxystearic and dihydroxybehenic acids.

In step c) of the process for preparing triglycerides containing dicarboxylic acids the organic phase obtained as the product of oxidative cleavage is fed to equipment suitable for separating free $C_5$-$C_{10}$ chain monocarboxylic acids (i) from the reaction mixture comprising triglycerides containing dicarboxylic acids (ii). The separation is advantageously performed by means of distillation processes. All distillation processes which do not give rise to strong thermal stress on the mixture of products obtained during step b), such as for example distillation in a flow of steam or in thin film evaporators, are preferred. Advantageously the evaporated mixture of monocarboxylic acids may be further subjected to distillation to obtain $C_5$-$C_{10}$ monocarboxylic acids having a greater degree of purity.

In a preferred form of the process the monocarboxylic acids are separated from the mixture containing the triglycerides through the use of a thin film evaporator.

One advantageous aspect of the process according to this invention lies in the fact that the distillation residue obtained at the end of step 2) is a high value product which can be directly used in elastomer compositions, for example for the production of tyres. Advantageously this residue finds use in elastomer compositions as an extender oil.

On the basis of the type of vegetable oils used for the preparation of triglycerides containing dicarboxylic acids, diesters of different $C_2$-$C_{24}$ dicarboxylic acids may be obtained, such as for example: oxalic acid, malonic acid, succinic acid, glutaric acid, adipic acid, pimelic acid, suberic acid, azelaic acid, sebacic acid, undecandicarboxylic acid, dodecandicarboxylic acid, brassylic acid, tetradecandicarboxylic acid or pentadecandicarboxylic acid. Suberic acid, azelaic acid, brassylic acid and their mixtures are particularly suitable for the purposes of this invention.

In a preferred form of the process according to the invention, mainly dibutyl azelate is obtained from esterifying triglycerides containing dicarboxylic acids prepared by oxidative cleavage from oils having a high oleic content with butanol.

The process according to this invention may be performed in either batch or continuous mode. Preferably the process is carried out in continuous mode.

The process according to the invention will now be described on the basis of non-limiting examples.

EXAMPLE 1 (TWO-STAGE ESTERIFICATION AND TRANSESTERIFICATION)

A mixture mainly comprising triglycerides having an azelaic acid content of 47% by weight obtained as a distillation residue after step c) of the process of oxidative cleavage described in Example 1 of WO2008/138892 (so-called "acid triglyceride") was used as the starting material.

The HPLC-MS analysis of the mixture revealed the presence of 94% of glycerides of formula $R_x$—O—$CH_2$—CH($OR_y$)—$CH_2$—O—$R_z$, according to the invention, wherein at least one of $R_x$, $R_y$ and/or $R_z$ is azelaic acid. The kinematic viscosity of the triglycerides mixture at 100° C. was 86.8 cSt.

Step 1)

The following were placed in a 1000 ml flask with a mechanical stirrer, thermometer and a Marcusson device for the collection of water:
 300 g of acid triglyceride
 1 g of 85% $H_3PO_4$
 50 g of n-butanol.

The flask was heated under reflux (internal temperature 160° C.); the water which formed from the condensation was distilled off, gradually adding a further 100 g of alcohol to compensate for that removed from the reaction equilibrium, in such a way as to maintain the temperature of the mixture around 160° C.

This was continued for 8 hours until water formation ceased.

The temperature was raised to 120° C. and the following were added to the flask:
 7 g of potassium t-butylate,
 150 g of butanol
and this was refluxed for 4 hours.

Step 2)

At the end the excess butanol was distilled off under reduced pressure, the residue was washed several times with water to recover the glycerine, it was dehydrated and distilled under vacuum at 1 mm Hg [approximately 133 Pa] to 270° C. in distillation apparatus. 250 g of distillate and 120 g of residue were obtained (corresponding to a ratio of distillate to the residue of 68/32).

The yield of dibutyl azelate calculated on the content in the distillate was 72%.

A polymer grade product was obtained by distillation in a 20 plate column.

EXAMPLE 2 (SINGLE STAGE ESTERIFICATION AND TRANSESTERIFICATION)

Step 1)

The following were placed in a 1000 ml flask with a mechanical stirrer, thermometer and Marcusson device to collect the water:
 300 g of acid triglyceride obtained as described in Example 1,
 1.5 g of 96% $H_2SO_4$,
 200 g of n-butanol.

The mixture was heated to an internal temperature of 135° C., distilling off the water which was formed from the condensation. The reaction was stopped after 2.5 hours when water ceased to be produced.

Step 2)

The excess butanol was evaporated off under vacuum, heating to approximately 70° C. in distillation apparatus; at the end of this the reaction mass was poured into a separating funnel, and the glycerine was allowed to separate out at ambient temperature.

The glycerine was separated off and the oily phase was washed with water until neutral pH.

The organic phase was dehydrated under vacuum, and then distilled under a vacuum of 1 mm Hg until it reached 270° C. in distillation apparatus.

290 g of distillate and 125 g of residue were obtained (corresponding to a ratio of distillate to the residue of 70/30).

The yield of dibutyl azelate calculated on the content in the distillate was 80%.

EXAMPLE 3 (SINGLE STAGE ESTERIFICATION AND TRANSESTERIFICATION)

Step 1)

The following were placed in a 1000 ml flask with a mechanical stirrer, thermometer and Marcusson device for the collection of water:
 200 g of acid triglyceride obtained as described in Example 1,
 1.0 g of 96% $H_2SO_4$,
 370 g of n-butanol.

The mixture was heated to an internal temperature of 135° C., distilling off the water formed by condensation. The reaction was stopped after 6 hours when water ceased to be produced.

Step 2)

The excess butanol was evaporated off under vacuum, heating to approximately 80° C. in distillation apparatus; on completion the reaction mass was poured into a separating funnel, and the glycerine was allowed to separate out at ambient temperature.

The glycerine was separated off and the oily phase was washed with water to neutral pH.

The organic phase was dehydrated under vacuum, and then distilled under a vacuum of 1 mm Hg until 270° C. was reached in distillation apparatus.

195 g of colourless distillate and 76 g of residue were obtained (corresponding to a ratio of distillate to the residue of 72/28).

The yield of dibutyl azelate calculated on the content of the distillate in comparison with the starting triglyceride content was 84%.

EXAMPLE 4 (SINGLE STAGE ESTERIFICATION AND TRANSESTERIFICATION)

Step 1)

A solution comprising:
 200 g of acid triglyceride obtained as described in Example 1
 370 g of n-butanol
were fed by means of a peristaltic pump into the bottom of a cylindrical reactor with a jacket heated to 115° C. and filled with 100 ml of Amberlyst 36 sulfonic resin; at the top of the column a distillation head collected the water/butanol azeotrope, while the liquid returned to circulation via the pump.

Circulation was continued until water ceased to be produced (approximately 4 hours).

Step 2)

The excess butanol was evaporated off under vacuum and the residue was treated as described in the preceding example.

A dibutyl azelate yield of 85% was obtained at the end of the distillation.

COMPARATIVE EXAMPLE

Example 1 of the patent application WO 2012/085012 was reproduced. The HPLC-MS analysis of the mixture of triglycerides after evaporation of the free carboxylic acids in a thin film evaporator revealed the presence of 43% (area) of glycerides of formula $Rx-R_x-O-CH_2-CH(OR_y)-CH_2-O-R_z$, according to the invention, wherein at least one of $R_x$, $R_y$ and/or $R_z$ is azelaic acid. The kinematic viscosity at 100° C. of the resulting mixture of triglycerides was 692 cSt.

An esterification with butyl alcohol catalysed by sulfuric acid was performed and the evaporation of volatile butyl esters allowed to obtain a ratio of distillate to the residue of merely 50/50.

The invention claimed is:

1. A process for preparing aliphatic dialkyl esters of saturated dicarboxylic acids from a triglycerides mixture containing
   at least one triglyceride of at least one saturated dicarboxylic acid and
   at least 65% of glycerides of formula $R_x-O-CH_2-CH(OR_y)-CH_2-O-R_z$, measured by HPLC-MS analysis
wherein $R_x$, $R_y$, $R_z$ are independently selected from the group consisting of H, $C_6$-$C_{24}$ monocarboxylic acid residues and $C_6$-$C_{24}$ dicarboxylic acid residues, and wherein at least one of $R_x$, $R_y$, $R_z$ is a $C_6$-$C_{24}$ dicarboxylic acid residue, the said process comprising the steps of:
   1) esterifying and/or transesterifying with an aliphatic alcohol said triglycerides mixture, in the presence of one or more catalysts capable of catalysing the esterifying and/or transesterifying;
   2) separating the aliphatic dialkyl esters of saturated dicarboxylic acids from the reaction mixture obtained at the end of step 1).

2. The process according to claim 1, in which said triglycerides mixture is obtained from vegetable oils containing unsaturated carboxylic acids.

3. The process according to claim 2, in which said triglycerides mixture is obtained by oxidative cleavage of the double bonds in the unsaturated carboxylic acids present in the vegetable oils.

4. The process according to claim 3, in which the oxidative cleavage is carried out through one or more oxidising agents selected from peroxides and $O_2$ or mixtures containing $O_2$.

5. The process according to claim 2, in which said triglycerides containing at least one dicarboxylic acid are prepared from vegetable oils containing triglycerides of unsaturated carboxylic acids, by means of the steps of:
   a) causing the triglycerides of unsaturated carboxylic acids to react with an oxidising compound in the presence of a catalyst capable of catalysing the reaction of oxidising of the olefin double bond in order to obtain an intermediate compound containing vicinal diols;
   b) causing the said intermediate compound to react with oxygen, or a gaseous mixture containing oxygen, with a catalyst capable of catalysing the reaction of oxidising the vicinal diols to carboxyl groups in order to obtain (i) saturated monocarboxylic acids and (ii) triglycerides containing saturated dicarboxylic acids;
   c) separating the saturated monocarboxylic acids (i) from the triglycerides containing saturated dicarboxylic acids (ii).

6. The process according to claim 1 in which step 1) is performed in a single stage and in the presence of a strong acid as catalyst.

7. The process according to claim 6 in which the strong acid is selected form sulfuric acid, hydrochloric acid, perchloric acid, alkylsulfonic acids, arylsulfonic acids, sulfonic resins or acid earths of the montmorillonite type.

8. The process according to claim 1 in which step 1) is performed using a weak acid to catalyse the esterification reaction in a first stage and a strong base to catalyse the transesterification reaction in a second stage.

9. The process according to claim 8 in which the weak acid is selected from the group comprising phosphoric acid, tungstic acid, molybdic acid, phosphotungstic acid or weakly acid montmorillonites and the strong base is selected from the group comprising sodium hydroxide, potassium hydroxide, sodium methylate or potassium t-butylate.

10. The process according to claim 1 in which the temperature of the esterification and transesterification reactions in step 1 is comprised between 80 and 200° C.

11. The process according to claim 1 in which the aliphatic alcohol is a straight or branched chain $C_1$-$C_{10}$ monoalcohol.

12. The process according to claim 11 in which the aliphatic alcohol is selected from methanol, ethanol, n-propanol or n-butanol.

13. The process according to claim 12 in which the aliphatic alcohol is n-butanol.

14. The process according to claim 1 in which said dicarboxylic acids present in the triglycerides in step 1) comprise at least one of oxalic acid, malonic acid, succinic acid, glutaric acid, adipic acid, pimelic acid, suberic acid, azelaic acid, sebacic acid, undecandicarboxylic acid, dodecandicarboxylic acid, brassylic acid, tetradecandicarboxylic acid or pentadecandicarboxylic acid.

15. The process according to claim 14 in which said dicarboxylic acids comprise azelaic acid.

16. The process according to claim 1 in which the aliphatic diesters of the dicarboxylic acids comprise dibutyl azelate.

17. The process according to claim 3, in which said triglycerides containing at least one dicarboxylic acid are prepared from vegetable oils containing triglycerides of unsaturated carboxylic acids, by means of the steps of:
   a) causing the triglycerides of unsaturated carboxylic acids to react with an oxidising compound in the presence of a catalyst capable of catalysing the reaction of oxidising of the olefin double bond in order to obtain an intermediate compound containing vicinal diols;
   b) causing the said intermediate compound to react with oxygen, or a gaseous mixture containing oxygen, with a catalyst capable of catalysing the reaction of oxidising the vicinal diols to carboxyl groups in order to obtain (i) saturated monocarboxylic acids and (ii) triglycerides containing saturated dicarboxylic acids;
   c) separating the saturated monocarboxylic acids (i) from the triglycerides containing saturated dicarboxylic acids (ii).

18. The process according to claim 4, in which said triglycerides containing at least one dicarboxylic acid are prepared from vegetable oils containing triglycerides of unsaturated carboxylic acids, by means of the steps of:
   a) causing the triglycerides of unsaturated carboxylic acids to react with an oxidising compound in the presence of a catalyst capable of catalysing the reaction of oxidising of the olefin double bond in order to obtain an intermediate compound containing vicinal diols;
   b) causing the said intermediate compound to react with oxygen, or a gaseous mixture containing oxygen, with a catalyst capable of catalysing the reaction of oxidising the vicinal diols to carboxyl groups in order to obtain (i) saturated monocarboxylic acids and (ii) triglycerides containing saturated dicarboxylic acids;

c) separating the saturated monocarboxylic acids (i) from the triglycerides containing saturated dicarboxylic acids (ii).

19. The process according to claim 2 in which step 1) is performed in a single stage and in the presence of a strong acid as catalyst.

20. The process according to claim 3 in which step 1) is performed in a single stage and in the presence of a strong acid as catalyst.

* * * * *